United States Patent
Poss et al.

(10) Patent No.: US 6,225,324 B1
(45) Date of Patent: May 1, 2001

(54) ANTIDEPRESSANT HETEROCYCLIC COMPOUNDS

(75) Inventors: Michael A. Poss, Lawrenceville; David R. Tortolani, Skillman, both of NJ (US); Ronald J. Mattson; Joseph P. Yevich, both of Southington, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/467,957

(22) Filed: Dec. 21, 1999

Related U.S. Application Data

(60) Provisional application No. 60/117,651, filed on Jan. 28, 1999.

(51) Int. Cl.[7] .................. A61K 31/445; C07D 401/04
(52) U.S. Cl. .................. 514/316; 514/212; 514/252; 514/256; 514/314; 514/318; 514/321; 514/326; 514/422; 540/596; 540/597; 540/602; 544/238; 544/333; 544/405; 546/176; 546/186; 546/187; 546/191; 546/193; 546/197; 546/208; 548/518
(58) Field of Search .................. 514/212, 252, 514/256, 314, 316, 318, 321, 326, 422; 540/596, 597, 602; 544/238, 333, 405; 546/176, 186, 193, 187, 197, 191, 208; 548/518

(56) References Cited

U.S. PATENT DOCUMENTS

| | | |
|---|---|---|
| 4,954,502 | 9/1990 | Smith et al. . |
| 4,957,921 | 9/1990 | Caprathe et al. . |
| 4,975,445 | 12/1990 | Caprathe et al. . |
| 5,352,678 | 10/1994 | Mattson et al. . |
| 5,387,593 | 2/1995 | Mattson et al. . |

FOREIGN PATENT DOCUMENTS

| | | |
|---|---|---|
| 560669 | 9/1993 | (EP) . |
| WO99/32481 | 7/1999 | (WO) . |
| WO99/51578 | 10/1999 | (WO) . |

OTHER PUBLICATIONS

Brouwer et al. "Two step sequential light–induced electro transfer in a simple . . . " CA 118:233400, 1993.*
Willemse et al. "Stepwise versus direct long range charge separation in molecular triads" CA 132:334117, 2000.*
Scherer, et al., "Synthesis and Exploratory Photophysical Investigation of Donor–Bridge–Acceptor Systems Derived from N–Substituted 4–Piperidones," *Recueil des Travaux Chimiques des Pays–Bas*, 112/10, pp. 535–548, Oct. 1993.
Eldred et al., "Orally Active Non–Peptide Fibrinogen Receptor (GpIIb/IIIa) Antagonists: Identification of 4–[4 [4–(Aminoimino–methyl)phenyl]–1–piperazinyl]–1–piperidineacetic Acid as a Long–Acting, Broad–Spectrum Antithrombotic Agent," *J. Med. Chem.*, 37, pp. 3882–3885, 1994.

* cited by examiner

Primary Examiner—Ceila Chang
(74) Attorney, Agent, or Firm—Richard P. Ryan

(57) ABSTRACT

Compounds of formula I are useful antidepressant agents

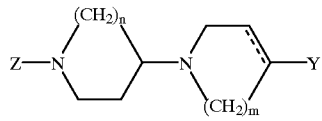

I demonstrating potent inhibition of 5-HT reuptake. Z is selected from among various phenyl and hetaryl moieties while Y is benzyl or indolyl.

9 Claims, No Drawings

ANTIDEPRESSANT HETEROCYCLIC COMPOUNDS

CROSS REFERENCE TO RELATED APPLICATION

This non-provisional application claims priority from provisional application U.S. Ser. No. 60/117,651 filed Jan. 28, 1999.

BACKGROUND OF THE INVENTION

This invention pertains to cyclic amino compounds having antidepressant and other psychotropic, bio-affecting properties and to their preparation and use. In some preferred embodiments, the invention is concerned with 1,3-disubstituted pyrrolidine, 1,4-disubstituted piperidine, or 1,4-disubstituted hexahydroazepine derivatives wherein the 3- or 4-substituent is benzyl, substituted benzyl, or substituted indolyl, and the 1-substituent is a 1-aryl-pyrrolidin-3yl, 1-aryl-piperidin-4-yl, or a 1-aryl-hexahydroazepin-4-yl moiety. These compounds and others structurally related thereto possess a unique serotonergic profile that makes them useful in the treatment of depression.

Mattson and Catt disclosed a series of piperazinyl- and piperidinyl-cyclohexanols characterized by structural formula A as anxiolytic agents in U.S. Pat. No. 5,387,593.

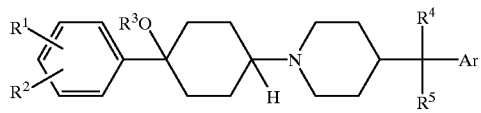

A

Mattson and Catt also disclosed a series of cyclohexylpiperazines and -piperidines characterized by structural formula B as antiischemic agents in U.S. Pat. No. 5,352,678.

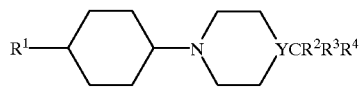

B

Mattson and Catt have also disclosed a series of piperazinyl- and piperidinyl-cyclohexenes and cyclohexanes characterized by structural formula C for treating ischemia-induced brain disorders in Eur. Pat. Appl., 560669, Sep. 15, 1993.

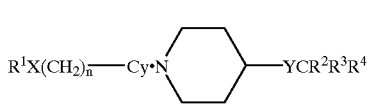

C

Scherer, et al. have disclosed the synthesis of some piperidinyl-piperidines, formula D, as as fluorescent probes (*Recl. Trav. Chim. Pays-Bas,* 112(10), 535–48, 1993).

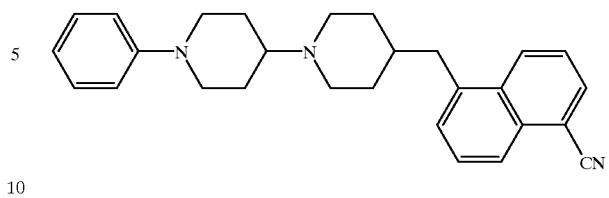

D

Eldred, et al. disclosed a series of antithrombotic agents characterized by the formula E in *Journal of Medicinal Chemistry,* Vol 37, pp 3882–5, 1994.

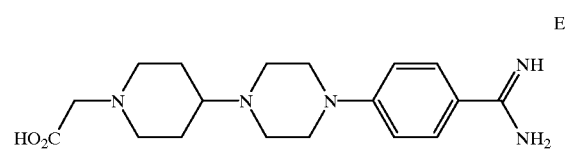

E

Caprathe, et al. disclosed a series of piperazinyl-cyclohexanol compounds characterized by structural formula F in U.S. Pat. No. 4,957,921. Formula F is:

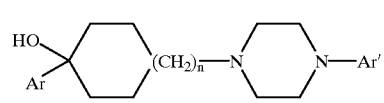

F

Caprathe, et al. disclosed a series of piperazinyl-cyclohexene compounds characterized by structural formula G in U.S. Pat. No. 4,975,445. Formula G is:

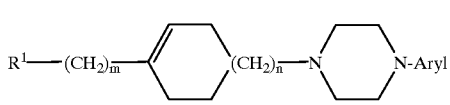

G

Smith, et al. in U.S. Pat. No. 4,954,502 disclosed a series of compounds of structural formula H having antidepressant properties. In these compounds A was, inter alia, a 5 to 7 carbon cycloalkanyl or cycloalkenyl ring.

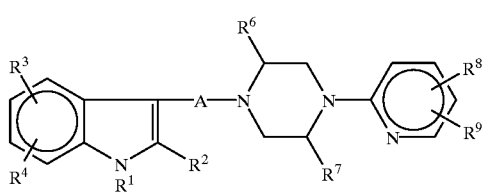

H

SUMMARY AND DESCRIPTION OF THE INVENTION

In its broadest aspect, the invention is concerned with certain compounds which are substituted-benzyl or substituted-indolyl cyclic amino- substituted N-aryl or heteroaryl cyclic amines that are useful for treating CNS disorders such as depression. The compounds conform to formula I:

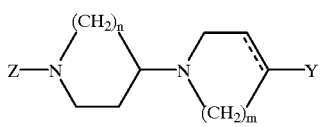

as well as pharmaceutically acceptable acid addition salts and/or hydrates thereof.

In formula I, Z is an aryl or hetaryl moiety selected from among phenyl, benzodioxane, benzodioxole, benzothiazole, pyridine, pyridazine, pyrimidine, and quinoline systems. These aryl or hetaryl rings can be unsubstituted or substituted with from one to three substituent groups selected from among $C_{1-4}$ alkyl, $C_{1-4}$ alkoxy, cyano and halo.

The solid and dotted lines in formula I denote a double or a single carbon-carbon covalent bond. The symbols m and n are independently selected from the integers 1 to 3.

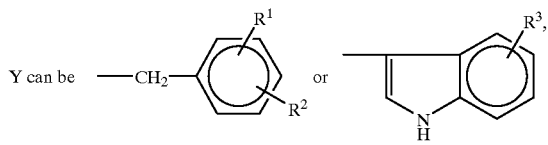

in which $R^1$ and $R^2$ are independently selected from hydrogen, halogen, or alkoxy; and $R^3$ can be hydrogen, halogen or cyano.

Halo or halogen refers to fluoride, chloride, bromide or iodide substituents with fluoride, chloride and bromide preferred.

Additionally, compounds of formula I also encompass all pharmaceutically acceptable acid addition salts and/or solvates thereof. The present invention is also considered to include stereoisomers including geometric as well as optical isomers, e.g. mixtures of enantiomers as well as individual enantiomers and diasteromers, which arise as a consequence or structural asymmetry in certain compounds of the instant series. Separation of the individual isomers is accomplished by application of various methods which are well known to practitioners in the art.

The term "$C_{1-4}$" refers to both straight and branched chain carbon radicals of from 1 to 4 carbon atoms inclusive. Illustrative of these radicals are carbon chains which can be methyl, ethyl, propyl, isopropyl, 1-butyl, 1-methylpropyl, 2-methylpropyl.

As can be seen, the formula I compounds comprise two sub-classes of compounds: 1) Y is a benzyl moiety and 2) Y is an indolyl moiety. Some preferred compounds are shown below.

Preferred compounds (INDOLE CMPDS):
1-{4-[4-(5-fluoroindol-3-yl)piperidyl]piperidyl}-2,4-dimethoxybenzene;
3-[1-(2H,3H-benzo[3,4-3]1,4-dioxan-6-yl)-4-piperidyl] 4-piperidyl]indole-5-carbonitrile;
3-{1-[1-(2,4-dimethoxyphenyl)-4-piperidyl]-4-piperidyl}indole-5-carbonitrile;
3-[1-(1-(5-quinolyl)-4-piperidyl)-4-piperidyl]indole-5-carbonitrile;
3-{1-[1-(2-methylbenzothiazol-5-yl)-4-piperidyl]-4-piperidyl}indole-5-carbonitrile;
3-{1-[1-(2,6-dimethoxyphenyl)-4-piperidyl]-4-piperidyl}indole-5-carbonitrile.

Preferred compounds (BENZYL CMPDS):
5-(4-{4-[(2-bromo-5-fluorophenyl)methyl] piperidyl}piperidyl)-2H-benzo[d]1,3-dioxolane;
5-(4-{4-[(2-bromo-5-methoxyphenyl)methyl] piperidyl}piperidyl) quinoline;
3-(4-{4-[(2-bromo-5-methoxyphenyl)methyl] piperidyl}piperidyl) benzenecarbonitrile;
2-(4-{4-[(2-bromo-5-methoxyphenyl)methyl] piperidyl}piperidyl) pyrimidine;
2-(4-{4-[(2-bromophenyl)methyl]piperidyl}piperidyl)-2,6-dimethoxybenzene;
3-(4-{4-[(2-bromo-5-methoxyphenyl)methyl] piperidyl}piperidyl)-6-chloropyridazine;
1-(4-{4-[(2,5-difluorophenyl)methyl]piperidyl}piperidyl)-4,5-dimethoxy-2-methylbenzene;
1-(4-{4-[(2-bromo-5-fluorophenyl)methyl] piperidyl}piperidyl)-4,5-dimethoxy-2-methylbenzene;
1-(4-{4-[(2,5-dichlorophenyl)methyl]piperidyl}piperidyl)-4,5-dimethoxy-2-methylbenzene;
2-(4-{4-[(2-bromophenyl)methyl]piperidyl}piperidyl)-1,3,5-trimethoxybenzene;
5-(4-{4-[(2-bromophenyl)methyl]piperidyl}piperidyl)-2-methoxypyridine;
5-(4-{4-[(2-chlorophenyl)methyl]piperidyl}piperidyl)-2-methoxypyridine;
5-(4-{4-[(2,5-difluorophenyl)methyl]piperidyl}piperidyl)-2-methoxypyridine;
5-(4-{4-[(2-bromo-5-fluorophenyl)methyl] piperidyl}piperidyl)-2-methoxypyridine;
5-(4-{4-[(2,5-dichlorophenyl)methyl]piperidyl}piperidyl)-2-methoxypyridine;
3-(4-{4-[(2,5-difluorophenyl)methyl]piperidyl}piperidyl)-4-methoxybenzenecarbonitrile;
4-methoxy-3-(4-{4-[(3-methoxyphenyl)methyl] piperidyl}piperidyl)benzenecarbonitrile;
3-(4-{4-[(2-bromo-5-fluorophenyl)methyl] piperidyl}piperidyl)-4-methoxybenzenecarbonitrile;
1-(4-{4-[(2,5-dichlorophenyl)methyl]piperidyl}piperidyl)-2,4,5-trimethoxybenzene;
8-(4-{4-[(2,5-dichlorophenyl)methyl]piperidyl}piperidyl)-7-methoxy-2H,3H,4H-benzo[b]1,5-dioxepin.

The pharmaceutically acceptable acid addition salts of the invention are those in which the counter ion does not contribute significantly to the toxicity or pharmacological activity of the salt and, as such, they are the pharmacological equivalents of the bases of formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid, preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, fumaric, mandelic, phosphoric, nitric, mucic, isethionic, palmitic, heptanoic, and others.

Compounds of formula I are most conveniently synthesized by the coupling (Reaction 1) of intermediates II and III under reductive alkylation conditions such as, titanium isopropoxide/NaBH$_4$, sodium cyanoborohydride, sodium triacetoxyborohydride and the like. Other methods known to those skilled in the art may also be used.

(Reaction 1)

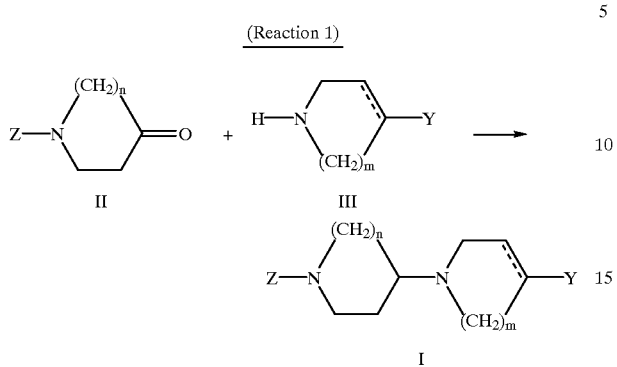

The compounds of formula I can also be prepared by the coupling (Reaction 1a) of N-protected ketone intermediate IIa with amine intermediate III to give intermediate IV under reductive alkylation conditions such as, titanium isopropoxide/NaBH$_4$, sodium cyanoborohydride, sodium triacetoxyborohydride and the like. Suitable protecting groups include t-butyloxycarbonyl, benzyloxycarbonyl, acetyl, formyl, and the like. The N-protecting group is then cleaved to give intermediate V using standard acidic, basic, or reductive conditions known to those skilled in the art. Intermediate V is then coupled with an appropriate heteroaryl halide using an appropriate base, such as sodium or potassium carbonate, ethanol, methanol, or the like, in solvents, such as acetonitrile, acetone, THF, or the like to give compounds of formula I. Intermediate V can also be condensed with phenyl bromides and other aryl bromides by the Buchwald reaction [Wolfe and Buchwald, *Tetrahedron Letters*, 38 (36), 6359 (1997)] to give compounds of formula I. Other methods known to those skilled in the art can also be used.

(Reaction 1a)

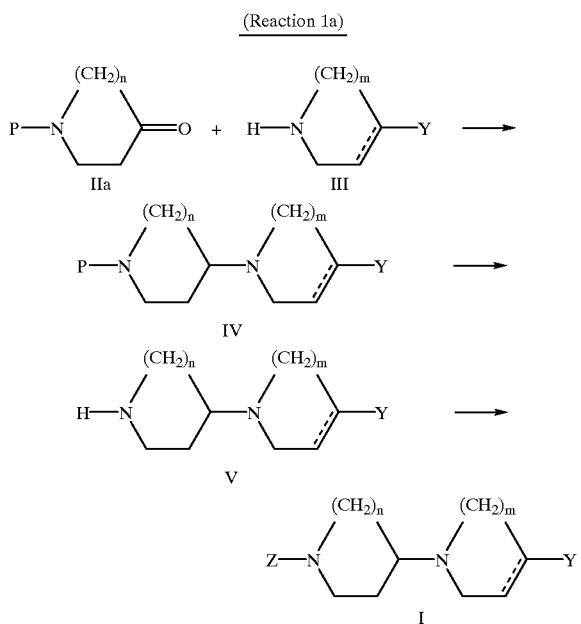

Intermediate Preparation: Formula II Compounds

Intermediate ketone compounds of formula II can be prepared by alkylation of an amine (1) with a dihaloalkanol (2) using an appropriate acid scavenger such as an alkali carbonate, e.g. K$_2$CO$_3$ in an appropriate organic solvent such as acetonitrile, acetone, THF, ethanol, methanol, or the like. Subsequent oxidation of (2) with an oxidizing agent such as DMSO/oxalyl chloride, pyridinium chlorochromate (PCC), pyridinium dichromate (PDC), or the like provides the formula II intermediate.

(Reaction 2)

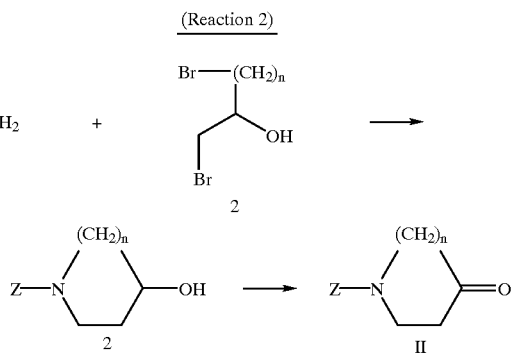

Methods other than Reaction 2 would be known to those skilled in the art for preparation of compounds of formula II. Some examples follow.

Alternatively, pyrrolidin-3-one intermediates of Formula II (n=1) can be prepared by coupling of a heteroaryl halide (4) with 3-pyrrolidinol (5) in Reaction 3. Such couplings can be done using an appropriate base, such as sodium or potassium carbonate, ethanol, methanol, or the like, in solvents, such as acetonitrile, acetone, THF, or the like. Subsequent oxidation of the intermediate pyrrolidinol (3) then provides the pyrrolidin-3-one of formula II. Such oxidations can be done using oxidizing agents, such as PCC, PDC, DMSO/oxalyl chloride, or the like. Other methods known to those skilled in the art may also be used.

(Reaction 3)

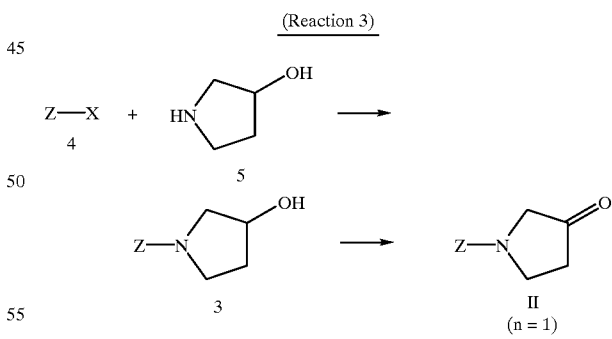

4-Piperidone intermediates of formula II (n=2) are most conveniently prepared in Reaction 4 of an aniline or heterocyclic amine (1) with quaternary alkyl ammonium salts of 4-piperidone (6; R=alkyl). Such reactions can be carried out using an appropriate base, such as sodium or potassium carbonate, or the like, in solvents, such as acetonitrile, acetone, THF, ethanol, methanol, or the like. Other methods known to those skilled in the art may also be used.

(Reaction 4)

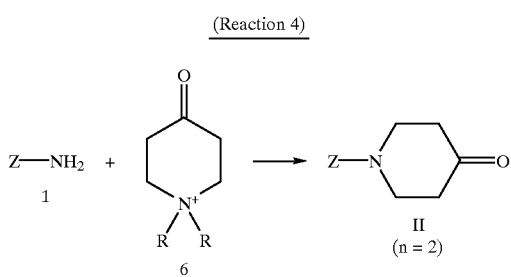

As shown in Reaction 5, 4-piperidone intermediates of formula II (n=2) can be prepared by the reaction of an aniline or heterocyclic amine (1) with esters of acrylic acid (7). The diester intermediate (8) is then reacted with a base, such as sodium or potassium alkoxides, sodium hydride, or the like, in solvents such as THF, diethyl ether, benzene, toluene, or the like, to give the keto-ester intermediate (9). Subsequent hydrolysis and decarboxylation of the keto-ester intermediate, under basic or acidic conditions known to those skilled in the art, gives the 4-piperidone intermediates of formula II (n=2). Other methods known to those skilled in the art may also be used.

(Reaction 5)

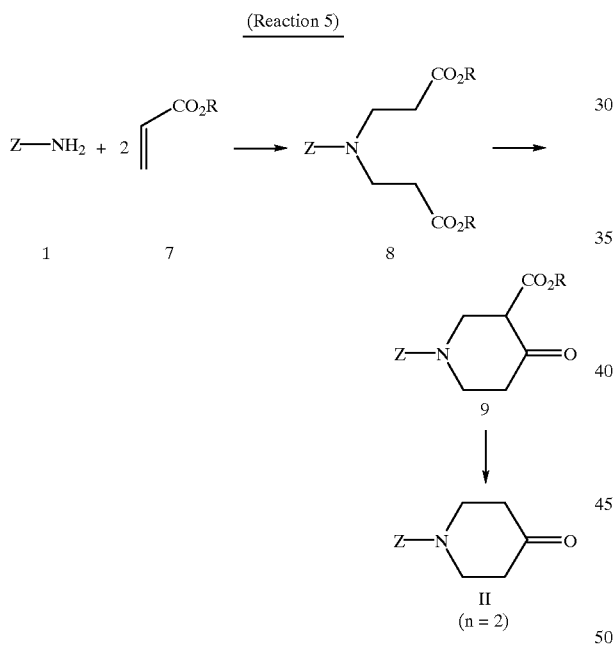

Alternatively, in Reaction 6 4-piperidone intermediates of formula II (n=2) can be prepared by coupling of a heteroaryl halide (4) with ketals of 4-piperidone (10; R=alkyl). Such couplings can be done using an appropriate base, such as sodium or potassium carbonate, ethanol, methanol, or the like, in solvents, such as acetonitrile, acetone, THF, or the like. Intermediate 10 can also be condensed with phenyl bromides and other aryl bromides by the Buchwald reaction [Wolfe and Buchwald, *Tetrahedron Letters*, 38 (36), 6359 (1997)] to give the 1-aryl intermediate (11). Subsequent cleavage of the intermediate 1-aryl ketal intermediate (11), then provides the 4-piperidone intermediates of formula II (n=2). Suitable acidic conditions for such cleavages include: dilute aqueous HCl, acetone/HCl, THF/HCl, acetone/ $H_2SO_4$, THF/$H_2SO_4$, dioxane/HCl, and the like. Acids suitable for this ketal hydrolysis include, but are not limited to, hydrochloric, sulfuric, acetic, phosphoric, paratoluene-sulfonic, methanesulfonic, benzoic and the like. Other methods known to those skilled in the art may also be used.

(Reaction 6)

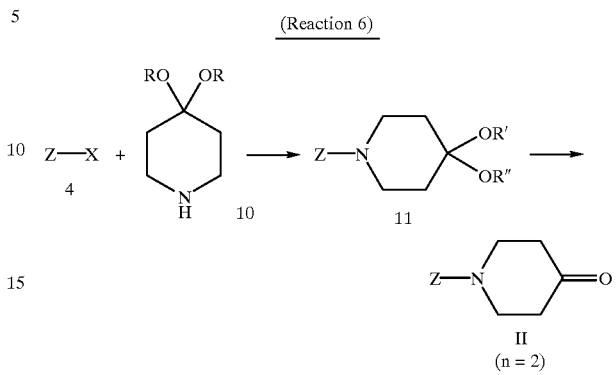

Azepin-4-one intermediates of formula II (n=3) are conveniently prepared by ring expansion (Reaction 7) of the corresponding 1-aryl-4-piperidone. Such ring expansions can be done using esters of diazoacetic acid, with Lewis acid catalysts such as $BF_3 \cdot Et_2O$ or the like, in solvents, such as diethyl ether, THF, or the like. Subsequent hydrolysis and decarboxylation of the keto-ester intermediate, under basic or acidic conditions known to those skilled in the art, then provides the azepin-4-one intermediates of formula II (n=3). Other methods known to those skilled in the art may also be used.

(Reaction 7)

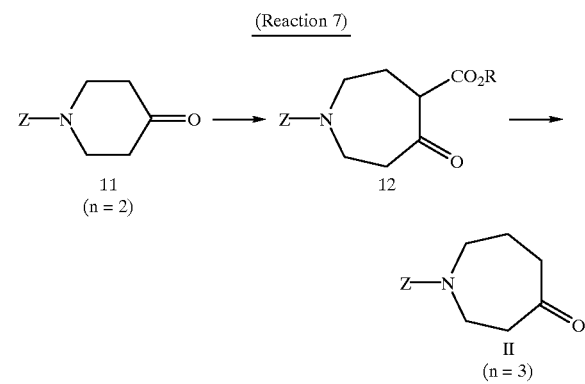

Intermediate Preparation: Formula III Compounds

The pyrrolidine intermediates of formula III (m=1) are conveniently prepared by monoalkylation of a 1-protected-pyrrolidin-2-one (13: R is alkyl, benzyl, etc.) with alkylating agents such as benzyl halides, tosylates, mesylates, or the like, using bases such as LDA, LiTMP, or the like, in solvents such as THF, diethyl ether, hexane, or the like, to give the benzyl pyrrolidinone intermediate (14). Suitable protecting groups include trimethylsilyl, methyl, benzyl, and the like. Alternatively, the 1-protected-pyrrolidin-2-one (13) can be condensed with a substituted benzaldehyde using bases such as NaH, LDA, LiTMP, sodium or potassium alkoxides, or the like, in solvents such as THF, diethyl ether, benzene, toluene, or the like. Subsequent reduction of the benzylidene intermediate (15: Ar is

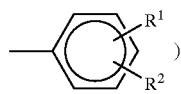

using hydrogen and platinum, palladium, or ruthenium catalysts, in solvents such as ethanol, ethyl acetate, or the like, provides the benzyl pyrrolidinone intermediate (14). Reduction of the benzyl pyrrolidinone intermediate (14) with reducing agents such as LAH, borane, alane, or the like, provides the 1-protected-pyrrolidine intermediate (16). Subsequent cleavage of the N-protecting group using methods known to those skilled in the art provides the pyrrolidine intermediates of formula III (m=1) as shown in Reaction 8.

(Reaction 8)

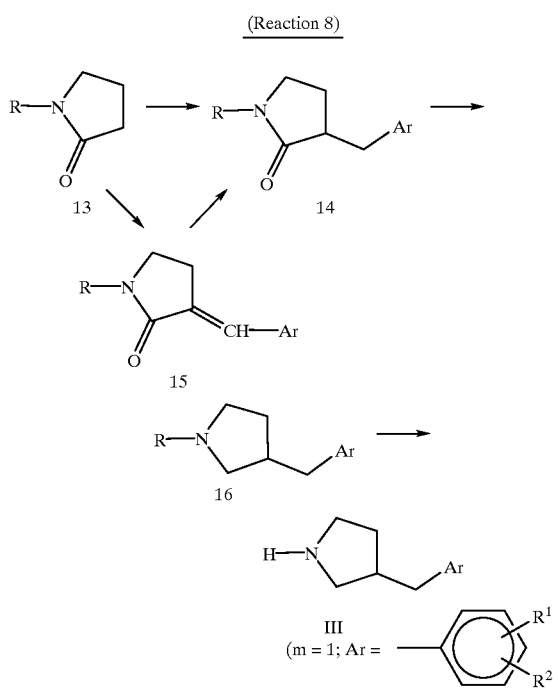

Alternatively, as shown in Reaction 9 an N-protected pyrrolidin-3-ol (17: P is an N-protecting group) can be oxidized to the pyrrolid-3-one (18). Condensation of ketone (18) with reagents such as benzyl phosphonate esters using bases such as NaH, LDA, sodium or potassium alkoxides, or the like, in solvents such as THF, diethyl ether, or the like, provides the benzylidene intermediate (19). Subsequent reduction of the benzylidene group using hydrogen and platinum, palladium, or ruthenium catalysts, in solvents such as ethanol, ethyl acetate, or the like, provides the N-protected pyrrolidine intermediate (16). The N-protecting group is then cleaved using methods known to those skilled in the art to give the pyrrolidine intermediates of formula III (m=1) as depicted in Reaction 9.

(Reaction 9)

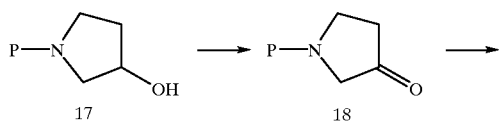

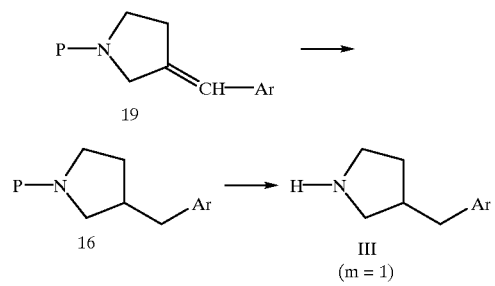

The piperidine intermediates of formula III (m=2) are conveniently prepared by condensation of an N-protected-4-piperidone (20) with reagents such as benzyl phosphonate esters using bases such as NaH, LDA, sodium or potassium alkoxides, or the like, in solvents such as THF, diethyl ether, or the like, provides the benzylidene intermediate (21). Subsequent reduction of the benzylidene group using hydrogen and platinum, palladium, or ruthenium catalysts, in solvents such as ethanol, ethyl acetate, or the like, provides the piperidine intermediate (22). The N-protecting group is then cleaved using methods known to those skilled in the art to give the piperidine intermediates of formula III (m=2) as depicted in Reaction 10.

(Reaction 10)

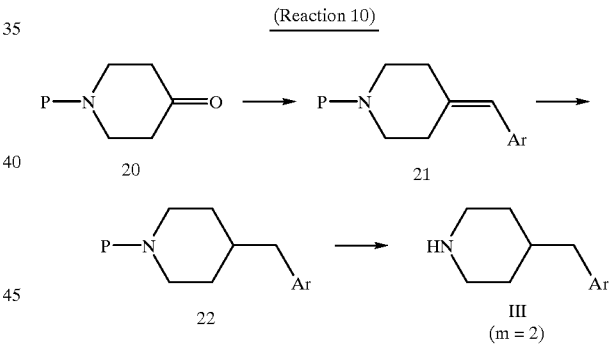

The piperidine intermediates of formula III (m=1; Y=3-indolyl) can be prepared by condensing an N-protected-4-piperidone (20) with a substituted indole using catalysts such as pyrrolidine, acetic acid, or the like, in solvents such as ethanol, benzene, THF, or the like, to give the the tetrahydropyridine intermediates (23). Cleavage of the N-protecting group provides the tetrahydropyridines of formula III (m=1; Y=3-indolyl). Alternatively, as shown in Reaction 11 the tetrahydropyridine intermediates (23) can be reduced using using hydrogen and a suitable catalyst such as platinum, palladium, or ruthenium catalysts, in solvents such as ethanol, ethyl acetate, or the like, to give the piperidine intermediates (24). The N-protecting group is then cleaved using methods known to those skilled in the art to give the piperidine intermediates of formula III (m=1; Y=3-indolyl).

(Reaction 11)

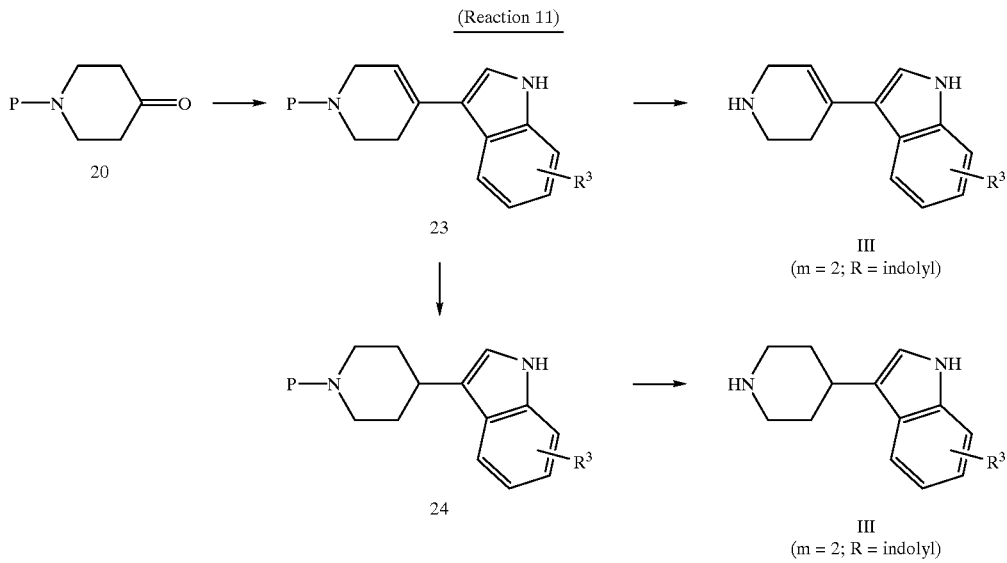

The 4-substituted azepine intermediates of formula III (m=3) are conveniently prepared by condensation of an N-protected-4-azepinone (25) with reagents such as benzyl phosphonate esters using bases such as NaH, LDA, sodium or potassium alkoxides, or the like, in solvents such as THF, diethyl ether, or the like, provides the benzylidene intermediate (26). Subsequent reduction of the benzylidene group using using hydrogen and platinum, palladium, or ruthenium catalysts, in solvents such as ethanol, ethyl acetate, or the like, provides the benzyl azepine intermediate (27). The N-protecting group is then cleaved using methods known to those skilled in the art to give the azepine intermediates of formula III (m=3) as shown in Reaction 12.

(Reaction 12)

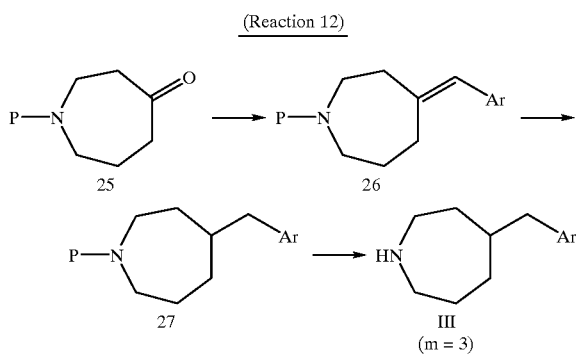

The reactions depicted above and their application are familiar to the practitioner skilled in organic synthesis and modifications of conditions and reagents would be readily understood. The skilled synthetic chemist would know how to adapt these processes for preparation of specific formula I compound including other compounds embraced by this invention but not specifically disclosed. Variations of the methods to produce the same compounds in somewhat different fashion will also be evident to one skilled in the art. To provide greater detail in description, representative synthetic examples are provided infra in the "Specific Embodiments" section.

The compounds of formula I show potent inhibition of 5-HT re-uptake and can be envisioned as potential agents for disorders associated with dysfunction in serotonergic neurotransmission. Such disorders may include depression, anxiety, eating disorders, obesity, and drug abuse. In particular, the active compounds of the instant series are envisioned as specific agents for treating depression.

The compounds comprising the present invention inhibit the re-uptake of endogenous serotonin. Selective inhibitors of serotonin uptake are effective for the treatment of mental depression and have been reported to be useful for treating chronic pain (see: R. W. Fuller, Pharmacologic Modification of Serotonergic Function: Drugs for the Study and Treatment of Psychiatric and Other Disorders," J. Clin. Psychiatry, 47:4 (Suppl.) April 1986, pp. 4–8). Compounds of the present invention are also envisioned to be useful in the following disorders: obsessive-compulsive disorder, feeding disorders, anxiety disorders and panic disorders.

Determination of endogenous monoaminergic re-uptake inhibition values both for serotonin and norepinephrine was accomplished using test methods described by P. Skolnick, et al., Br. J. Pharmacology, (1985), 86, pp. 637–644; with only minor modifications. In vitro $IC_{50}$ (nM) test values were determined for representative compounds of Formula I based on their inhibition of synaptosomal re-uptake of tritiated serotonin. Test data $IC_{50}$ values lower than 500 nM are considered to reflect activity as an inhibitor of serotonin re-uptake. Compounds with $IC_{50}$ values lower than 100 nM comprise preferred compounds and those with $IC_{50}$ value less than 10 nM are most preferred.

Another aspect of the instant invention provides a method for treating a mammal afflicted with depression or chronic pain which comprises administering systemically to said mammal a therapeutically effective amount of a compound of formula I or a pharmaceutically acceptable acid addition salt thereof.

The administration and dosage regimen of compounds of formula I are considered to be done in the same manner as for the reference compound fluoxetine, cf: Schatzberg, et al., J. Clin. Psychopharmacology 7/6 Suppl. (1987) pp. 4451–4495, and references therein. Although the dosage and dosage regimen must in each case be carefully adjusted, utilizing sound professional judgement and considering the age, weight and condition of the recipient, the route of administration and the nature and gravity of the illness, generally the daily dose will be from about 0.05 to about 10 mg/kg, preferably 0.1 to 2 mg/kg, when administered parenterally and from about 1 to about 50 mg/kg, preferably about 5 to 20 mg/kg, when administered orally. In some instances, a sufficient therapeutic effect can be obtained at lower doses while in others, larger doses will be required. Systemic administration refers to oral, rectal and parenteral (i.e. intramuscular, intravenous and subcutaneous). Generally, it will be found that when a compound of the present invention is administered orally, a larger quantity of the active agent is required to produce the same effect as a similar quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents. Therapeutically, they are generally given as pharmaceutical compositions comprised of an antidepressant amount of a compound of formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a formula I compound with conventional pharmaceutical vehicles are employed for parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonance (NMR) spectral characteristics refer to chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as broad singlet (bs), singlet (s), multiplet (m), heptet (hept), quartet (q), triplet (t) or doublet (d). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$).

Analytical thin-layer chromatography (TLC) was performed on 0.25 mm EM silica gel 60 F-254 coated glass plates and preparative flash chromatography was performed on EM silica gel (36–62 $\mu$m). The solvent systems used are reported where appropriate. All reaction, extraction and chromatography solvents were reagent grade and used without further purification except tetrahydrofuran (THF) which was distilled from sodium/benzophenone ketyl. All nonaqueous reactions were carried out in flame-dried glassware under a nitrogen atmosphere.

A. Synthesis of Intermediates

Compounds of Formula II

EXAMPLE 1

1-(3-Cyanophenyl)-3-pyrrolidinone

A mixture of 3-aminobenzonitrile (3.0 g, 25.4 mmol) 1,4dibromobutan-2-ol (8.8 g, 4.4 ml, 38.1 mmole), potassium carbonate (7.7 g, 55.7 mmole), and triethyl phosphite (20 ml) was heated to 130° C. for 18 hr. The mixture was cooled, diluted with water, and extracted twice with ethyl ether. The ether extracts were dried over magnesium sulfate and concentrated in vacuo. The residue was purified by chromatography on silica gel using ethyl acetate/hexane (25% to 67% gradient) as the eluent to give 1-(3-cyanophenyl)-3-pyrrolidinol (7.4 g, 50%).

A solution of 1-(3-cyanophenyl)-3-pyrrolidinol (0.65 g, 4.1 mmol) in triethyl amine (5.72 ml, 41 mmol) and DMSO (15 ml) was cooled to 0° C. and pyridine-SO$_3$ (1.96 g, 12.3 mmol) was added. The mixture was stirred at 0° C. for 1 hr and at room temperature for 18 hr. The reaction mixture was poured into water (100 ml) and extracted three times with methylene chloride. The methylene chloride extracts were dried over magnesium sulfate and concentrated in vacuo to give 1-(3-cyanophenyl)-3-pyrrolidinone (0.41 g, 54%) that was used without purification.

Also prepared by this general method were:
1 -(2,6-dimethoxyphenyl)-3-pyrrolidinone.

EXAMPLE 2

1-(Benzodioxol-5-yl)-4-piperidone

A slurry of 1-benzyl-4-piperidone methiodide (5.43 g, 16.4 mmol) in water (10 ml) was added over 30 min to a gently refluxing mixture of 5-amino-benzodioxole (1.86 g, 13.6 mmol) and potassium carbonate (0.2 g, 1.4 mmol) in ethanol (25 ml). Water (25 ml) was added portion wise over 30 min, and the mixture was heated to reflux for an additional 30 min. The mixture was cooled and the ethanol removed in vacuo. Water (25 ml) was added and the mixture was extracted twice with methylene chloride (25 ml). The organic extracts were combined, dried over Na$_2$SO$_4$, and concentrated in vacuo. The crude product was purified by chromatography on silica gel using CHCl$_3$ as the eluent to give the 1 -(Benzodioxol-5-yl)-4-piperidone (2.0 g, 67%). MS (esi): 220 (M+H)$^+$. $^1$H-NMR (300 MHz, CDCl$_3$): $\delta$2.56 (t, 4H), 3.44 (t, 4H), 5.92 (s, 2H), 6.44 (dd, 1H), 6.60 (d, 1H), 6.74 (d, 1H).

Also prepared by this general method were:
1-(2-methoxyphenyl)-4-piperidone, 32% yield;
1-(2,3-dimethoxyphenyl)-4-piperidone;
1-(3,4-dimethoxyphenyl)-4-piperidone, 55% yield;
1-(2,4-dimethoxyphenyl)-4-piperidone;
1-(2,5-dimethoxyphenyl)-4-piperidone, 44% yield;
1-(2,6-dimethoxyphenyl)-4-piperidone, 18% yield;
1-(3-cyanophenyl)-4-piperidone, 28% yield;
1-(3-chloro-4-cyanophenyl)-4-piperidone, 48% yield;
1-(3-fluoro-4-methoxyphenyl)-4-piperidone, 28% yield;
1-(3-fluoro-2-methoxyphenyl)-4-piperidone;
1-(benzothiazol-5-yl)-4-piperidone;
1-(2-methylbenzothiazol-5-yl)-4-piperidone, 100% yield;

1-(quinolin-4-yl)-4-piperidone;
1-(quinolin-5-yl)-4-piperidone;
1-(2,3-dihydro-1,4-benzodioxan-6-yl)-4-piperidone, 99% yield;
1-(4,5-dimethoxy-2-methylphenyl)-4-piperidone;
1-(1,3,5-trimethoxyphenyl)-4-piperidone;
1-(2-methoxypyridin-5-yl)-4-piperidone;
1-(2,4,5-trimethoxyphenyl)-4-piperidone;
1-(7-methoxy-2H,3H ,4H-benzo[b]1,5-dioxepin-8-yl)-4-piperidone.

EXAMPLE 3

1-(6-chloropyrimidin4-yl)-4-piperidone

A mixture of 4-piperidone ethylene ketal (7.15 g, 50 mmol), 4,6-dichloropyrimidine (7.45 g, 50 mmol), and potassium carbonate (10 g) in acetonitrile (75 ml) was stirred for 18 hr and then heated to reflux for 1 hr. The mixture was cooled and filtered. The filtrate was concentrated in vacuo to give a white solid. The crude 1-(6-chloropyrimidin-4-yl)-4-piperidone ethylene ketal was recrystallized from c-hexane to give white powder (11.7 g, 92%, mp: 112–114° C.).

A solution of 1-(6-chloropyrimidin-4-yl)-4-piperidone ethylene ketal (2 g, 7.83 mmol) in acetone (25 ml) and 1 N HCl (25 ml) was stirred for 18 hr. The acetone was removed in vacuo and the mixture made basic with saturated sodium carbonate. The mixture was extracted twice with ethyl acetate. The extracts were combined, dried with brine, and concentrated in vacuo to give 1-(6-chloropyrimidin-4-yl)-4-piperidone as a white powder (1.6 g, 96.6%, mp: 100–103° C.).
Also prepared by this general method were:
1-(2-chloropyrimidin-4-yl)-4-piperidone;
1-(6-chloropyrazin-2-yl)-4-piperidone;
1-(6-chloropyridazin-3-yl)-4-piperidone;
1-(5-cyanopyridin-2-yl)-4-piperidone;
1-(4-cyanophenyl)-4-piperidone, 48%;
1-(3-chloro-4-cyanophenyl)-4-piperidone, 48%;

EXAMPLE 4

1-(6-methoxypyrimidin-4-yl)-4-piperidone

A solution of 1-(6-chloropyrimidin-4-yl)-4-piperidone ethylene ketal (2g, 8.87 mmol), sodium methoxide (prepared from 0.8 g sodium metal, 34.8 mmol), in methanol (50 ml) was heated to reflux for 17 hr. The mixture was cooled and concentrated in vacuo. The crude 1-(6-methoxypyrimidin-4-yl)-4-piperidone ethylene ketal was washed with water, filtered, and air dried (1.42 g, 63.8%, 81–82.5° C.).

A solution of 1-(6-methoxypyrimidin4-yl)-4-piperidone ethylene ketal (1.38 g, 5.5 mmol) in acetone (25 ml) and 1 N HCl (25 ml) was stirred for 18 hr. The acetone was removed in vacuo and the mixture made basic with saturated sodium carbonate. The mixture was extracted twice with ethyl acetate. The extracts were combined, dried with brine, and concentrated in vacuo to give 1-(6-methoxypyrimidin-4-yl)-4-piperidone as a white powder (0.95 g, 83.5%, mp: 111–114° C.).
Also prepared by this general method were:
1-(2-methoxypyrimidin-4-yl)-4-piperidone;
1-(6-methoxypyrazin-2-yl)-4-piperidone;
1-(6-methoxypyridazin-3-yl)-4-piperidone.

EXAMPLE 5

1-(pyrimidin-4-yl)-4-piperidone

A solution of 1-(6-chloropyrimidin-4-yl)-4-piperidone ethylene ketal (2 g, 8.87 mmol) in ethanol (25 ml) and ethyl acetate (25 ml) was hydrogenated at 60 psi for 1 hr over 10% Pd/C (0.25 g). The mixture was filtered and the filtrate was concentrated in vacuo. The residue was dissolved in methylene chloride and filtered through celite. The filtrate was concentrated in vacuo to give 1-(pyrimidin-4-yl)-4-piperidone ethylene as a white solid (112–115° C.).

The 1-(pyrimidin-4-yl)-4-piperidone ethylene ketal was dissolved in acetone (25 ml) and 1 N HCl (25 ml) was stirred for 18 hr. The acetone was removed in vacuo and the mixture made basic with saturated sodium carbonate. The mixture was extracted twice with ethyl acetate. The extracts were combined, dried with brine, and concentrated in vacuo to give 1-(pyrimidin-4-yl)-4-piperidone as a white powder (0.80 g, 51.4% for two steps, mp: 61–65° C.).
Also prepared by this general method were:
1-(pyrazin-2-yl)-4-piperidone;
1-(pyridazin-3-yl)-4-piperidone.

EXAMPLE 5A 1-(5-cyano-2-methoxyphenyl)-4-piperidone 1,4-Dioxa-8-azaspiro[4.5]decane (1.47 g, 10.28 mmol), sodium bis(trimethylsilyl)amide (1 N in THF, 12 ml), and $PdCl_2(p(o\text{-tolyl})_3)_2$ [2 mol % catalyst prepared from bis (acetonitrile) Pd(II) chloride(53 mg, 0.206 mmol) and tri(o-tolyl)phosphine (125 mg, 0.52 mmol)] were added to a solution of 3-bromo-4-methoxybenzonitrile (1.82 g, 8.58 mmol) in toluene (40 ml). The reaction was stirred for 5 hours at 100° C. The reaction was concentrated in vacuo, diluted with water, and extracted with methylene chloride. The organic extract was concentrated in vacuo, and the residue purified by chromatography on silica gel using hexane/ethyl acetate (80/20) as the eluent to give 1-(5-cyano-2-methoxyphenyl)-4-piperidone ethylene ketal (900 mg, 38%). This ketal was dissolved in dioxane (15 ml) and HCl (6 N, 2.2 ml) and stirred at 100° C. for 2 h. The solution was cooled, quenched with saturated aqueous $NaHCO_3$. The mixture was extracted with methylene chloride, concentrated in vacuo, and purified by chromatography on silica gel using hexane/ethyl acetate (80/20) as the eluent to give 1-(5-cyano-2-methoxyphenyl)-4-piperidone (125 mg, 19%).

Compounds of Formula III

EXAMPLE 6

3-(2-bromobenzyl)pyrrolidine 1-(Trimethylsilyl)-2-pyrrolidinone (7.39 g, 51.7 mmol) was added slowly to a solution of lithium diisopropylamide (25 ml, 2 M in heptane/THF/ ethylbenzene, 50 mmol) and THF (10 ml) at −78° C. The solution was stirred for 1 hr, and 2-bromobenzyl bromide (6 ml, 46.5 mmol) was added dropwise. The solution was stirred for 2 hr and quenched with 1 N HCl. The organic layer was separated, washed with water, and concentrated in vacuo. The residue was dissolved in methanol, and heated to reflux with HCl (5 ml of 37%) and tetrabutylammonium fluoride (10 ml of 1 M in THF, 10 mmol), for 15 min. The solution was made basic with saturated $NA_2CO_3$ and concentrated in vacuo. The residue was dissolved in $CHCl_3$, washed with water, and concentrated in vacuo to give an oil. This crude product was purified by chromatography on silica gel using 5% methanol/$CH_2Cl_2$ as the eluent to give 3-(2-bromobenzyl) pyrrolidin-3-one as an oil (9.5 g, 80.4%).

A solution of 3-(2-bromobenzyl)pyrrolidin-3-one (5.0 g, 19.7 mmol) in THF (10 ml) was added slowly to a solution of AlH3 (freshly prepared from 1 M LAH in THF (50 ml) and 98% $H_2SO_4$ (1.3 ml) at 0° C.). The mixture was stirred for 4 hr, cooled to 0° C., and slowly quenched with water and 10 N NaOH. The mixture was diluted with ether and filtered. The filtrate was washed with brine and concentrated in vacuo to an oil. The oil was purified by short path vacuum distillation to give 3-(2-bromobenzyl)pyrrolidine as an oil (3.2 g, 67.7%).

Also prepared by this general method was:
3-(2,5-difluoro)benzyl)pyrrolidine.

EXAMPLE 7

4-(2-bromobenzyl)piperidine

A solution of dimethyl 2-bromobenzylphosphonate (45.66 g, 148.9 mmol) in THF was added slowly to a mixture of NaH (7.14 g of a 60% mineral oil dispersion, 178.5 mmol) in THF (200 ml) and the mixture was stirred for 1 hr. A solution of 1-(tert-butoxycarbonyl)-4-piperidinone (29.67 g, 148.9 mmol) in THF was added dropwise and the mixture was heated to reflux for 1.5 hr. The mixture was cooled and quenched with brine. The mixture was diluted with ethyl acetate, washed with water, and dried with brine. The organic layer was concentrated in vacuo to an oil. The oil was dissolved in acetonitrile and extracted with hexane. The acetonitrile layer was concentrated in vacuo to give 1-(tert-butoxycarbonyl)-4-[(2-bromophenyl) methylene]piperidine as an oil that solidified upon standing (48.3 g, 97%).

A solution of 1-(tert-butoxycarbonyl)-4-[(2-bromophenyl)methylene]-piperidine (8 g, 22.7 mmole) in ethyl acetate (75 ml) and ethanol (75 ml) was shaken with $PtO_2$ (0.75 g) and hydrogen (60 psi) for 15 min. Two further batches of 1-(tert-butoxycarbonyl)-4-[(2-bromophenyl)-methylene]-piperidine (8 g each, 24 g total) were similarly reduced and the mixtures were filtered. The filtrates were combined and concentrated in vacuo. The residue was dissolved in dioxane (200 ml) and 3 N HCl (100 ml) and stirred for 18 hr. The solution was concentrated in vacuo and the residue was made basic with 50% sodium hydroxide. The mixture was extracted with $CH_2Cl_2$. The extracts were dried over $Na_2SO_4$ and concentrated in vacuo to give a yellow oil that was purified by short path vacuum distillation to give 4-(2-bromobenzyl)piperidine as a oil (15 g, 86.6%). The oil converted to the fumarate salt using fumaric acid (6.85 g) in 2-propanol to give 4-(2-bromobenzyl)piperidine fumarate as a white solid (15.8 g, 62.6% overall, mp: 164–165° C.).

Also prepared by this general method were:
4-(2-bromo-5-fluorobenzyl)piperidine;
4-(2-bromo-5-methoxybenzyl)piperidine;
4-(2,5-dichlorobenzyl)piperidine;
4-(2-chlorobenzyl)piperidine.

EXAMPLE 8 hexahydro-4 H-4-(2-bromobenzyl)azepine

Di-tert-butyl dicarbonate (4.1 g, 18.7 mmol) was added to a stirred solution of hexahydro-4 H-azepin-4-one (2.8 g, 18.7 mmol) and $NaHCO_3$ (1.6 g, 18.7 mmol) in water (70 ml) and $CH_2Cl_2$ (70 ml). The mixture was stirred for 20 hr. The organic layer was separated, dried over $Na_2SO_4$, and concentrated in vacuo to give 1-(tert-butyloxycarbonyl)-hexahydro-4 H-azepin-4-one as an amber oil (3.98 g, 100%).

A solution of dimethyl 2-bromobenzylphosphonate (5.5 g, 18.7 mmol) in THF was added slowly to a mixture of NaH (0.8 g of a 60% mineral oil dispersion, 20 mmol) in THF (75 ml) and ethanol (0.5 ml) and the mixture was stirred for 45 min. A solution of 1-(tert-butyloxycarbonyl)-hexahydro-4 H-azepin-4-one (3.98 g, 18.7 mmol) in THF was added dropwise and the mixture was heated to reflux for 5 hr. The mixture was cooled and quenched with water. The mixture was diluted with ethyl acetate, washed with water, and dried with brine. The organic layer was concentrated in vacuo. The residue was purified by chromatography on silica gel using 5% ethyl acetate/hexane to give 1-(tert-butoxycarbonyl)-4-[(2-bromophenyl)methylene]-hexahydro4 H-azepine as a clear oil that solidified upon standing (4.3 g, 62.8%).

A solution of 1-(tert-butoxycarbonyl)-4-[(2-bromophenyl)methylene]-hexahydro-4 H-azepine (4.3 g, 11.7 mmol) in ethyl acetate (50 ml) and ethanol (30 ml) was shaken with $PtO_2$ (0.4 g) and hydrogen (60 psi) for 15 min. The mixture was filtered and the filtrate was concentrated in vacuo. The residue was dissolved in dioxane (100 ml) and 2 N HCl (50 ml. The solution was stirred for 18 hr, and then concentrated in vacuo. The residue was made basic with saturated $NA_2CO_3$. The mixture was extracted with $CH_2Cl_2$. The organic extracts were dried over $Na_2SO_4$ and concentrated in vacuo. The residue was converted to the fumarate salt in 2-propanol to give hexahydro-4 H-4-(2-bromobenzyl) azepine fumarate as a white powder (2.5 g, 79.7%, mp: 148–150° C.).

B. Synthesis of Formula I Products

EXAMPLE 9

5-(4-{4-[(2-bromo-5-fluorophenyl)methyl] piperidyl}piperidyl)-2 H-benzo[d]1,3-dioxolane A solution of 1-(benzodioxol-5-yl)-4-piperidone (1.5 g, 6.84 mmol) and 4-(2-bromo-5-fluorobenzyl)piperidine (2.4 g, 8.89 mmol) and sodium triacetoxy-borohydride (2.5 g, 11.63 mmol) in THF (25 ml) and acetic acid (0.39 ml) was stirred over 4 Å sieves for 18 hr. The mixture was filtered. 1 N NaOH (10 ml) was added to the filtrate, which was then concentrated in vacuo. The residue was dissolved in $CHCl_3$ (50 ml) and extracted with water. The $CHCl_3$ layer was concentrated in vacuo to give an oil (4.2 g) which was crystallized from isopropyl ether. This crude product was purified by chromatography on silica gel using 30% acetone/ $CH_2Cl_2$ as the eluent to give 5-(4-{4-[(2-bromo-5-fluorophenyl)methyl]piperidyl}piperidyl)-2 H-benzo[d]1,3-dioxolane (1.2 g, 37%). This material was converted to the dihydrochloride salt (mp: 272–273° C.).

Also prepared by this general method were:
2-(4-{4-[(2-bromophenyl)methyl]piperidyl}piperidyl)-1,3-dimethoxybenzene;
3-(4-{4-[(2-bromo-5-methoxyphenyl)methyl] piperidyl}piperidyl)-6-chloropyridazine;
5-(4-{4-[(2-bromo-5-methoxyphenyl)methyl] piperidyl}piperidyl) quinoline;
3-(4-{4-[(2-bromo-5-methoxyphenyl) methyl] piperidyl}piperidyl) benzenecarbonitrile;
2-(4-{4-[(2-bromo-5-methoxyphenyl)methyl] piperidyl}piperidyl) pyrimidine;
1-{4-[4-(5-fluoroindol-3-yl)piperidyl]piperidyl}2,4-dimethoxybenzene;
3-[1-(1-(2 H,3 H-benzo[3,4-3]1,4-dioxan-6-yl)-4-piperidyl) 4-piperidyl]indole-5-carbonitrile;
3-{-[1-(2,4-dimethoxyphenyl)-4-piperidyl]-4-piperidyl}indole-5-carbonitrile;
3-[1-(1-(5-quinolyl)-4-piperidyl)-4-piperidyl]indole-5-carbonitrile;

3-{1-[1-(2-methylbenzothiazol-5-yl)-4-piperidyl]-4-piperidyl}indole-5-carbonitrile;
3-{1[1-(2,6-dimethoxyphenyl)-4-piperidyl]-4-piperidyl}indole-5-carbonitrile;
1-(4-{4-[(2,5-difluorophenyl)methyl]piperidyl}piperidyl)-4,5-dimethoxy-2-methylbenzene;
1-(4-{4-[(2-bromo-5-fluorophenyl)methyl]piperidyl}piperidyl)-4,5-dimethoxy-2-methylbenzene;
1-(4-{4-[(2,5-dichlorophenyl)methyl]piperidyl}piperidyl)-4,5-dimethoxy-2-methylbenzene;
2-(4-{4-[(2-bromophenyl)methyl]piperidyl}piperidyl)-1,3,5-trimethoxybenzene;
5-(4-{4-[(2-bromophenyl)methyl]piperidyl}piperidyl)-2-methoxypyridine;
5-(4-{4-[(2-chlorophenyl)methyl]piperidyl}piperidyl)-2-methoxypyridine;
5-(4-{4-[(2,5-difluorophenyl)methyl]piperidyl}piperidyl)-2-methoxypyridine;
5-(4-{4-[(2-bromo-5-fluorophenyl)methyl]piperidyl}piperidyl)-2-methoxypyridine;
5-(4-{4-[(2,5-dichlorophenyl)methyl]piperidyl}piperidyl)-2-methoxypyridine;
3-(4-{4-[(2,5-difluorophenyl)methyl]piperidyl}piperidyl)-4-methoxybenzenecarbonitrile;
4-methoxy-3-(4-{4-[(3-methoxyphenyl)methyl]piperidyl}piperidyl)benzenecarbonitrile;
3-(4-{4-[(2-bromo-5-fluorophenyl)methyl]piperidyl}piperidyl)-4-methoxybenzenecarbonitrile;
1-(4-{4-[(2,5-dichlorophenyl)methyl]piperidyl}piperidyl)-2,4,5-trimethoxybenzene;
8-(4-{4-[(2,5-dichlorophenyl)methyl]piperidyl}piperidyl)-7-methoxy-2 H,3 H,4 H-benzo[b]1,5-dioxepin.

EXAMPLE 10

2-(4-{4-[(2,5-Dichlorophenyl)methyl] piperidinyl}hexahydro-4 H-azepine)pyrimidine A solution of 1-(tert-butyloxycarbonyl)-hexahydro-4 H-azepin-4-one (650 mg, 3 mol), 4-(2,5-dichlorobenzyl)piperidine (732 mg, 2.24 mmol), sodium triacetoxyborohydride (825 mg, 3.9 mmol), acetic acid (0.17 ml, 3 mmol), and trimethyl orthoformate (0.640 ml, 6 mmol) in dichloroethane (5 ml) was stirred for 36 hr at room temperature. The reaction was quenched with 1 N NaOH and stirred for 2 hr. The mixture was extracted with methylene chloride. The methylene chloride extracts were dried over magnesium sulfate and concentrated in vacuo. The residue was purified by chromatography on silica gel using ethyl acetate/isopropanol as the eluent to give 1-(tert-butyloxycarbonyl)-4-{[(2,5-dichlorophenyl)methyl]piperid-1-yl}hexahydro-4 H-azepine (889 mg, 67%).

A solution of 1-(tert-butyloxycarbonyl)-4-{[(2,5-dichlorophenyl)methyl]piperid-1-yl}hexahydro4 H-azepine (700 mg, 1.58 mmol) in trifluoroacetic acid (2 ml) and methylene chloride (0.5 ml) was stirred at room temperature for 15 min. The solution was concentrated in vacuo and the residue was dissolved in chloroform and extracted with saturated aqueous sodium carbonate. The chloroform extract was dried over sodium sulfate and concentrated in vacuo to give 4-{[(2,5-dichlorophenyl)methyl]piperid-1-yl}hexahydro-4 H-azepine (489 mg, 90%).

A mixture of 4-{[(2,5-dichlorophenyl)methyl]piperid-1-yl}hexahydro-4 H-azepine (236 mg, 0.69 mmol), 2-chloropyridine (237 mg, 2.07 mmol), and potassium carbonate (190 mg, 1.38 mmol) in dimethyl formamide (5 ml) was heated to 70° C. for 20 or. The mixture was diluted with water and extracted three times with ethyl acetate. The combined ethyl acetate extracts were extracted with water five times and dried with brine and sodium sulfate. The extracts were concentrated in vacuo and the residue purified by chromatography on silica gel using methylene chloride/methanol as the eluent to give 2-(4-{4-[(2,5-dichlorophenyl)methyl]piperidinyl}hexahydro-4 H-azepine)pyrimidine (198 mg, 69%).

Also prepared by this general method were:

2-(4-{4-[(2-bromophenyl)methyl]piperidinyl}hexahydro-4 H-azepine)pyrimidine, 47%;
2-(4-{4-[(2,5-dichlorophenyl)methyl] piperidinyl}hexahydro-4 H-azepine)-3-chloropyridazine, 65%;
2-(4-{4-[(2-bromophenyl)methyl]piperidinyl}hexahydro-4 H-azepine)-3-chloropyridazine, 29%.

EXAMPLE 11

Serotonin Transporter Binding Assay

Tissue Preparation. HEK-293 cells that stably express human serotonin transporters (HEK-hSERT cells) were grown at 37° C. in 5% $CO_2$ as a monolayer in medium consisting of EMEM supplemented with 10% fetal bovine serum and G418 sulfate (500 μg/ml). To prepare membranes for radioligand binding experiments, cells were rinsed twice with phosphate-buffered saline (138 mM NaCl, 4.1 mM KCl, 5.1 mM $Na_2PO_4$, 1.5 mM $KH_2PO_4$, 11.1 mM glucose, pH 7.4). Cells were transferred from plates to polypropylene tubes (16×100 mm), centrifuged at 1,200×g for 5 min and were frozen at −80° C. until assay. Following centrifugation, pellets were resuspended by homogenization in buffer consisting of 50 mM Tris (pH 7.7 at 25° C.), 120 mM NaCl and 5 mM KCl and then centrifuged at 32,000×g for 10 min. Following centrifugation, supernatants were discarded and pellets were resuspended in buffer consisting of 50 mM Tris (pH 7.4 at 25° C.), 150 mM NaCl and 5 mM KCl.

High-affinity binding assay. Membrane homogenates (200 μl/plate) were incubated with 1 nM [$^3$H]-citalopram (specific activity=85 Ci/mmol) and increasing concentrations of test compounds for 1 hour at 25° C. total volume of 250 μl. The assay buffer consisted of 50 mM Tris pH 7.4 at 25° C.), 120 mM NaCl and 5 mM KCl (pH 7.4 with conc. (HCl). Plates were incubated for 1 hour at 25° C., then filtered through 0.5% PEI treated Whatman GF/B filters using a Brandel cell harvester. Filters were washed three times with 3 ml of ice-cold tris wash buffer. Non-specific binding was defined with 10 μM fluoxetine.

Data analysis. Amount of radioligand bound in the presence and absence of competitor was analyzed by plotting (−)log drug concentration versus the amount of radioligand specifically bound. The midpoint of the displacement curve ($IC_{50}$, nM), signifies the potency. $K_i$ values were calculated using the method of Cheng and Prusoff (1973).

Substances which inhibit the re-uptake of serotonin are recognized to be effective antidepressants (Selective Serotonin Reuptake Inhibitors. Edited by J P Feighner and W F Boyer, Chichester, England. John Wiley & Sons 1991, pp 89–108). The following compounds inhibit the re-uptake of serotonin with Ki<100 nM:

TABLE 1

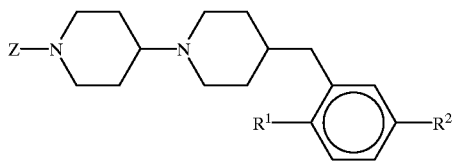

| Example # | Z | R¹ | R² | Yield % |
|---|---|---|---|---|
| 12 | benzodioxan-6-yl | I | methoxy | 33 |
| 13 | 3,4-dimethoxyphenyl | Cl | Cl | 41 |
| 14 | 3-fluoro-4-methoxyphenyl | Cl | Cl | 47 |
| 15 | benzodioxol-5-yl | Cl | Cl | 26 |
| 16 | benzodioxan-6-yl | Cl | Cl | 22 |
| 17 | 3,4-dimethoxyphenyl | F | F | 62 |
| 18 | 3-fluoro-4-methoxyphenyl | F | F | 61 |
| 19 | benzodioxol-5-yl | F | F | 66 |
| 20 | benzodioxan-6-yl | F | F | 70 |
| 21 | 3,4-dimethoxyphenyl | Br | H | 47 |
| 22 | 3-fluoro-4-methoxyphenyl | Br | H | 47 |
| 23 | benzodioxol-5-yl | Br | H | 48 |
| 24 | benzodioxan-6-yl | Br | H | 50 |
| 25 | 2-methoxyphenyl | F | F | 43 |
| 26 | 2,5-dimethoxyphenyl | F | F | 52 |
| 27 | quinolin-6-yl | F | F | 74 |
| 28 | quinolin-5-yl | F | F | 61 |
| 29 | 2-methoxyphenyl | Br | H | 32 |
| 30 | 2,5-dimethoxyphenyl | Br | H | 40 |
| 31 | quinolin-6-yl | Br | H | 29 |
| 32 | quinolin-5-yl | Br | H | 8 |
| 33 | 2-methoxyphenyl | Cl | H | 58 |
| 34 | 2,5-dimethoxyphenyl | Cl | H | 34 |
| 35 | 2,4-dimethoxyphenyl | Cl | H | 59 |
| 36 | quinolin-6-yl | Cl | H | 66 |
| 37 | quinolin-5-yl | Cl | H | 43 |
| 38 | 3-fluoro-4-methoxyphenyl | Cl | H | 30 |
| 39 | benzodioxol-5-yl | Cl | H | 30 |
| 40 | benzodioxan-6-yl | Cl | H | 42 |
| 41 | 2,5-dimethoxyphenyl | H | methoxy | 3 |
| 42 | 3,4-dimethoxyphenyl | H | methoxy | 7 |
| 43 | 3-fluoro-4-methoxyphenyl | H | methoxy | 7 |
| 44 | 2-methoxyphenyl | Br | F | 25 |
| 45 | 2,5-dimethoxyphenyl | Br | F | 37 |
| 46 | quinolin-6-yl | Br | F | 33 |
| 47 | 3-fluoro-4-methoxyphenyl | Br | F | 21 |
| 48 | benzodioxol-5-yl | Br | F | 34 |
| 49 | benzodioxan-6-yl | Br | F | 24 |
| 50 | 2,5-dimethoxyphenyl | F | methoxy | 30 |
| 51 | quinolin-6-yl | F | methoxy | 26 |
| 52 | 3,4-dimethoxyphenyl | F | methoxy | 14 |
| 53 | 3-fluoro-4-methoxyphenyl | F | methoxy | 11 |
| 54 | 2-methoxyphenyl | Br | methoxy | 31 |
| 55 | 2,5-dimethoxyphenyl | Br | methoxy | 25 |
| 56 | 2,4-dimethoxyphenyl | Br | methoxy | 27 |
| 57 | quinolin-6-yl | Br | methoxy | 21 |
| 58 | quinolin-5-yl | Br | methoxy | 18 |
| 59 | 3,4-dimethoxyphenyl | Br | methoxy | 17 |
| 60 | benzodioxol-5-yl | Br | methoxy | 17 |
| 61 | benzodioxan-6-yl | Br | methoxy | 21 |
| 62 | 2,3-dimethoxyphenyl | Cl | H | 33 |
| 63 | 2,3-dimethoxyphenyl | Br | H | 37 |
| 64 | 3-fluoro-2-methoxyphenyl | Br | F | 6 |
| 65 | 2-methoxyphenyl | Cl | Cl | 28 |
| 66 | 2,5-dimethoxyphenyl | Cl | Cl | 59 |
| 67 | 2,4-dimethoxyphenyl | Cl | Cl | 35 |
| 68 | 2,3-dimethoxyphenyl | Cl | Cl | 23 |
| 69 | 3-chloro-4-fluorophenyl | Cl | H | 13 |
| 70 | 3-chloro-4-fluorophenyl | F | F | 22 |
| 71 | 3-chloro-4-fluorophenyl | Br | H | 20 |
| 72 | 3-chloro-4-fluorophenyl | H | methoxy | 5 |
| 73 | 3-chloro-4-fluorophenyl | Br | F | 17 |
| 74 | 3-chloro-4-fluorophenyl | F | methoxy | 21 |
| 75 | 3-chloro-4-fluorophenyl | Br | methoxy | 17 |
| 76 | 3-chloro-4-fluorophenyl | Cl | Cl | 24 |
| 77 | 2-methyl-benzothiazol-5-yl | Cl | H | 19 |
| 78 | 2-methyl-benzothiazol-5-yl | F | F | 69 |
| 79 | 2-methyl-benzothiazol-5-yl | Br | H | 26 |

TABLE 1-continued

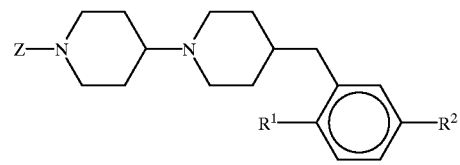

| Example # | Z | R¹ | R² | Yield % |
|---|---|---|---|---|
| 80 | 2-methyl-benzothiazol-5-yl | H | methoxy | 11 |
| 81 | 2-methyl-benzothiazol-5-yl | Br | F | 5 |
| 82 | 2-methyl-benzothiazol-5-yl | F | methoxy | 32 |
| 83 | 2-methyl-benzothiazol-5-yl | Br | methoxy | 11 |
| 84 | 2-methyl-benzothiazol-5-yl | Cl | Cl | 19 |
| 85 | benzothiazol-6-yl | Cl | H | 26 |
| 86 | benzothiazol-6-yl | F | F | 25 |
| 87 | benzothiazol-6-yl | Br | H | 12 |
| 88 | benzothiazol-6-yl | Br | F | 4 |
| 89 | benzothiazol-6-yl | F | methoxy | 21 |
| 90 | benzothiazol-5-yl | Br | methoxy | 3 |
| 91 | benzothiazol-5-yl | Cl | Cl | 18 |
| 92 | 3-cyanophenyl | Cl | H | 17 |
| 93 | 3-cyanophenyl | F | F | 10 |
| 94 | 3-cyanophenyl | Br | H | 22 |
| 95 | 3-cyanophenyl | H | methoxy | 7 |
| 96 | 3-cyanophenyl | Br | F | 25 |
| 97 | 3-cyanophenyl | F | methoxy | 31 |
| 98 | 3-cyanophenyl | Br | methoxy | 12 |
| 99 | 3-cyanophenyl | Cl | Cl | 33 |
| 100 | 4-cyanophenyl | Cl | H | 12 |
| 101 | 4-cyanophenyl | F | F | 27 |
| 102 | 4-cyanophenyl | Br | H | 20 |
| 103 | 4-cyanophenyl | H | methoxy | 2 |
| 104 | 4-cyanophenyl | Br | F | 15 |
| 105 | 4-cyanophenyl | F | methoxy | 12 |
| 106 | 4-cyanophenyl | Cl | Cl | 16 |
| 107 | 3-chloro-4-cyanophenyl | Cl | H | 14 |
| 108 | 3-chloro-4-cyanophenyl | F | F | 24 |
| 109 | 3-chloro-4-cyanophenyl | Br | H | 13 |
| 110 | 3-chloro-4-cyanophenyl | H | methoxy | 14 |
| 111 | 3-chloro-4-cyanophenyl | Br | F | 16 |
| 112 | 3-chloro-4-cyanophenyl | F | methoxy | 17 |
| 113 | 3-chloro-4-cyanophenyl | Br | methoxy | 23 |
| 114 | 3-chloro-4-cyanophenyl | Cl | Cl | 19 |
| 115 | pyrimidin-2-yl | Cl | H | 21 |
| 116 | pyrimidin-2-yl | F | F | 42 |
| 117 | pyrimidin-2-yl | Br | H | 28 |
| 118 | pyrimidin-2-yl | H | methoxy | 3 |
| 119 | pyrimidin-2-yl | Br | F | 41 |
| 120 | pyrimidin-2-yl | F | methoxy | 13 |
| 121 | pyrimidin-2-yl | Br | methoxy | 32 |
| 122 | pyrimidin-2-yl | Cl | Cl | 32 |
| 123 | 2-chloropyrimidin-4-yl | Cl | H | 22 |
| 124 | 2-chloropyrimidin-4-yl | F | F | 20 |
| 125 | 2-chloropyrimidin-4-yl | Br | H | 10 |
| 126 | 2-chJoropyrimidin-4-yl | Br | F | 23 |
| 127 | 2-chloropyrimidin-4-yl | Br | methoxy | 17 |
| 128 | 2-chloropyrimidin-4-yl | Cl | Cl | 29 |
| 129 | 2,6-dimethoxyphenyl | Cl | H | 33 |
| 130 | 2,6-dimethoxyphenyl | F | F | 67 |
| 131 | 2,6-dimethoxyphenyl | Br | H | 16 |
| 132 | 2,6-dimethoxyphenyl | Br | F | 9 |
| 133 | 2,6-dimethoxyphenyl | Br | methoxy | 21 |
| 134 | 2,6-dimethoxyphenyl | Cl | Cl | 15 |
| 135 | 2-methoxypyrimidin-4-yl | Cl | H | 19 |
| 136 | 2-methoxypyrimidin-4-yl | Br | H | 13 |
| 137 | 2-methoxypyrimidin-4-yl | H | methoxy | 9 |
| 138 | 2-methoxypyrimidin-4-yl | Br | F | 7 |
| 139 | 2-methoxypyrimidin-4-yl | Br | methoxy | 9 |
| 140 | 2-methoxypyrimidin-4-yl | Cl | Cl | 13 |
| 141 | 6-chloropyridazin-3-yl | Cl | H | 12 |
| 142 | 6-chloropyridazin-3-yl | F | F | 17 |
| 143 | 6-chloropyridazin-3-yl | Br | H | 11 |
| 144 | 6-chloropyridazin-3-yl | H | methoxy | 5 |
| 145 | 6-chloropyridazin-3-yl | Br | F | 19 |
| 146 | 6-chloropyridazin-3-yl | F | methoxy | 17 |
| 147 | 6-chloropyridazin-3-yl | Br | methoxy | 3 |

TABLE 1-continued

| Example # | Z | R¹ | R² | Yield % |
|---|---|---|---|---|
| 148 | 6-chloropyridazin-3-yl | Cl | Cl | 14 |
| 149 | pyrimidin-4-yl | Cl | H | 15 |
| 150 | pyrimidin-4-yl | Br | H | 19 |
| 151 | pyrimidin-4-yl | Br | F | 28 |
| 152 | pyrimidin-4-yl | Br | methoxy | 14 |
| 153 | pyrimidin-4-yJ | Cl | Cl | 30 |
| 154 | 6-methoxypyrimidin-4-yl | Cl | H | 8 |
| 155 | 6-methoxy-pyrimidin-4-yl | Br | H | 6 |
| 156 | 6-methoxypyrimidin-4-yl | H | methoxy | 6 |
| 157 | 6-methoxypyrimidin-4-yl | Br | F | 20 |
| 158 | 5-cyanopyridin-2-yl | Cl | H | 12 |
| 159 | 5-cyanopyridin-2-yl | F | F | 13 |
| 160 | 5-cyanopyridin-2-yl | Br | H | 32 |
| 161 | 5-cyanopyridin-2-yl | H | methoxy | 2 |
| 162 | 5-cyanopyridin-2-yl | Br | F | 23 |
| 163 | 5-cyanopyridin-2-yl | Cl | Cl | 15 |
| 164 | pyrazin-2-yl | Cl | H | 22 |
| 165 | pyrazin-2-yl | Br | H | 12 |
| 166 | pyrazin-2-yl | Br | F | 16 |
| 167 | 6-methoxypyrazin-2-yl | F | F | 20 |
| 168 | 6-methoxypyrazin-2-yl | Br | H | 22 |
| 169 | 6-methoxypyrazin-2-yl | H | methoxy | 11 |
| 170 | 6-methoxypyrazin-2-yl | Cl | Cl | 14 |
| 171 | 6-chloropyrazin-2-yl | Cl | H | 11 |
| 172 | 6-chloropyrazin-2-yl | F | F | 25 |
| 173 | 6-chloropyrazin-2-yl | Br | H | 15 |
| 174 | 6-chloropyrazin-2-yl | H | methoxy | 7 |
| 175 | 6-chloropyrazin-2-yl | Br | F | 13 |
| 176 | 6-chloropyrazin-2-yl | F | methoxy | 14 |
| 177 | 6-chloropyrazin-2-yl | Br | methoxy | 9 |
| 178 | 6-chloropyrazin-2-yl | Cl | Cl | 21 |
| 179 | 5-chloro-2-methoxyphenyl | Br | F | 19 |
| 180 | 2,4,6-trimethoxyphenyl | Br | F | 23 |
| 181 | 6-methoxypyrazin-2-yl | Br | methoxy | 4 |
| 182 | pyrazin-2-yl | Cl | Cl | 23 |
| 183 | 6-methoxypyrimidin-4-yl | Cl | Cl | 11 |
| 184 | 6-methoxypyrimidin-4-yl | F | F | 15 |

Additional analogs were synthesized using the aforementioned methods and were shown to inhibit the re-uptake of serotonin with Ki<100 nM. Examples of these analogs are displayed in Table 2.

TABLE 2

| Example # | Z | n | m | R¹ | R² | Yield % |
|---|---|---|---|---|---|---|
| 185 | 3-cyanophenyl | 1 | 2 | Br | H | 37 |
| 186 | 3-cyanophenyl | 1 | 2 | Cl | H | 26 |
| 187 | 2,6-dimethoxyphenyl | 1 | 2 | Cl | Cl | 56 |
| 188 | 2,6-dimethoxyphenyl | 1 | 2 | Br | H | 32 |
| 189 | 2,6-dimethoxyphenyl | 1 | 2 | Cl | H | 43 |
| 190 | pyrimidin-2-yl | 3 | 2 | Cl | Cl | 69 |
| 191 | 6-chloropyridazin-3-yl | 3 | 2 | Cl | Cl | 65 |
| 192 | 6-chloropyridazin-3-yl | 3 | 2 | Br | H | 29 |
| 193 | pyrimidin-2-yl | 3 | 2 | Br | H | 47 |

TABLE 2-continued

| Example # | Z | n | m | R¹ | R² | Yield % |
|---|---|---|---|---|---|---|
| 194 | 6-chloropyridazin-3-yl | 2 | 1 | Br | H | 71 |
| 195 | benzodioxol-5-yl | 2 | 1 | F | F | 65 |
| 196 | benzodioxol-5-yl | 2 | 1 | Br | H | 93 |
| 197 | 2,6-dimethoxyphenyl | 2 | 3 | Br | H | 22 |
| 198 | benzodioxol-5-yl | 2 | 3 | Br | H | 74 |
| 199 | 4,5-dimethoxy-2-methylphenyl | 2 | 2 | F | F | 19 |
| 200 | 4,5-dimethoxy-2-methylphenyl | 2 | 2 | Br | F | 21 |
| 201 | 4,5-dimethoxy-2-methylphenyl | 2 | 2 | Cl | Cl | 15 |
| 202 | 2,4,6-trimethoxyphenyl | 2 | 2 | Br | H | 59 |
| 203 | 2-methoxypyridin-5-yl | 2 | 2 | Br | H | 30 |
| 204 | 2-methoxypyridin-5-yl | 2 | 2 | Cl | H | 24 |
| 205 | 2-methoxypyridin-5-yl | 2 | 2 | F | F | 56 |
| 206 | 2-methoxypyridin-5-yl | 2 | 2 | Br | F | 25 |
| 207 | 2-methoxypyridin-5-yl | 2 | 2 | Cl | Cl | 2 |
| 208 | 5-cyano-2-methoxyphenyl | 2 | 2 | Cl | Cl | 16 |
| 209 | 5-cyano-2-methoxyphenyl | 2 | 2 | H | OMe | 15 |
| 210 | 5-cyano-2-methoxyphenyl | 2 | 2 | Br | F | 11 |
| 211 | 2,4,5-trimethoxyphenyl | 2 | 2 | Cl | Cl | 14 |
| 212 | 7-methoxy-2H,3H,4H-benzo[b]1,5-dioxepin-8-yl | 2 | 2 | Cl | Cl | 38 |

Similarly, Table 3 displays examples of the indole class of compounds that were synthesized and tested and found to have Ki values <100 nM.

TABLE 3

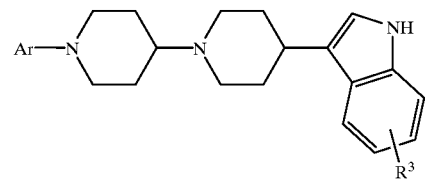

| Example # | Ar | R³ | Yield % |
|---|---|---|---|
| 213 | 2,3-dimethoxyphenyl | 5-cyano | 16 |
| 214 | 2,4-dimethoxyphenyl | 5-fluoro | 27 |
| 215 | 2,4-dimethoxyphenyl | 5-cyano | 21 |
| 216 | 2,5-dimethoxyphenyl | 5-fluoro | 27 |
| 217 | 2,5-dimethoxyphenyl | 5-cyano | 24 |
| 218 | 2,6-dimethoxyphenyl | 5-cyano | 14 |
| 219 | 2-chloropyrimidin-4-yl | 5-cyano | 14 |
| 220 | 2-methoxyphenyl | 5-fluoro | 20 |
| 221 | 2-methoxyphenyl | 5-cyano | 11 |
| 222 | 2-methoxypyrimidin-4-yl | 5-cyano | 30 |
| 223 | 2-methyl-benzothiazol-5-yl | 5-cyano | 25 |
| 224 | 3-chloro, 4-cyanophenyl | 5-cyano | 16 |
| 225 | 3-cyanophenyl | 5-fluoro | 16 |
| 226 | 3-cyanophenyl | 5-cyano | 17 |
| 227 | 3-fluoro, 4-methoxyphenyl | 5-cyano | 21 |
| 228 | 3-fluoro, 4-methoxyphenyl | 5-fluoro | 8 |
| 229 | 4-cyanophenyl | 5-fluoro | 4 |
| 230 | 4-cyanophenyl | 5-cyano | 3 |
| 231 | 5-cyano-pyrid-2-yl | 5-fluoro | 22 |
| 232 | 5-cyanopyridin-2-yl | 5-cyano | 16 |

TABLE 3-continued

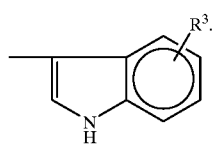

| Example # | Ar | R³ | Yield % |
|---|---|---|---|
| 233 | 6-chloropyrazin-2-yl | 5-fluoro | 15 |
| 234 | 6-chloropyrazin-2-yl | 5-cyano | 7 |
| 235 | 6-chloropyridazin-3-yl | 5-cyano | 7 |
| 236 | 6-methoxypyrazin-2-yl | 5-cyano | 13 |
| 237 | benzodioxan-6-yl | 5-fluoro | 15 |
| 238 | benzodioxan-6-yl | 5-cyano | 20 |
| 239 | benzodioxol-5-yl | 5-fluoro | 12 |
| 240 | benzodioxol-5-yl | 5-fluoro | 5 |
| 241 | benzothiazol-6-yl | 5-cyano | 2 |
| 242 | pyrazin-2-yl | 5-cyano | 20 |
| 243 | pyrimidin-2-yl | 5-cyano | 18 |
| 244 | quinolin-5-yl | 5-fluoro | 5 |
| 245 | quinolin-5-yl | 5-cyano | 27 |
| 246 | quinolin-6-yl | 5-cyano | 12 |

What is claimed is:

1. A compound of formula I and its pharmaceutically acceptable salts

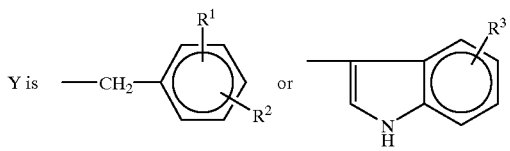

I and/or hydrates thereof wherein

Z is selected from phenyl, benzodioxolone, benzodioxole, benzothiazole, pyridine, pyridazine, pyrimidine, and quinoline moieties that are unsubstituted or optimally substituted with one to three substituents selected from $C_{1-4}$ alkyl, $C_{1-4}$ alkoxy, cyano, and halo;

the solid and dotted lines denote either a double or a single covalent bond;

m and n are independently integers 1 to 3; and

Y is 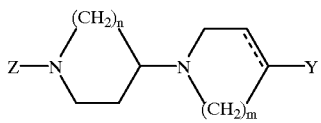 or 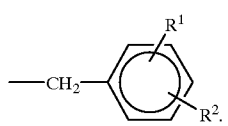

in which $R^1$ and $R^2$ are independently selected from hydrogen, halogen or alkoxy and $R^3$ is hydrogen, halogen or cyano.

2. The compound of claim 1 wherein Y is

3. The compound of claim 1 wherein Y is

4. A compound of claim 3 selected from
1-{4-[4-(5-fluoroindol-3-yl)piperidyl]piperidyl}-2,4-dimethoxybenzene;
3-[1-(1-(2 H,3 H-benzo[3,4-3]1,4-dioxan-6-yl)-4-piperidyl)4-piperidyl]indole-5-carbonitrile;
3-{1-[1-(2,4-dimethoxyphenyl)-4-piperidyl]-4-piperidyl}indole-5-carbonitrile;
3-[1-(1-(5-quinolyl)-4-piperidyl)-4-piperidyl]indole-5-carbonitrile;
3-{1-1-(2-methylbenzothiazol-5-yl)-4-piperidyl]-4-piperidyl}indole-5-carbonitrile;
3-{1-[1-(2,6-dimethoxyphenyl)-4-piperidyl]-4-piperidyl}indole-5-carbonitrile.

5. A compound of claim 2 selected from
5-(4-{4-[(2-bromo-5-fluorophenyl)methyl]piperidyl}piperidyl)-2 H-benzo[d]1,3-dioxolane;
5-(4-{4-[(2-bromo-5-methoxyphenyl)methyl]piperidyl}piperidyl) quinoline;
3-(4-{4-[(2-bromo-5-methoxyphenyl)methyl]piperidyl}piperidyl) benzenecarbonitrile;
2-(4-{4-[(2-bromo-5-methoxyphenyl)methyl]piperidyl}piperidyl) pyrimidine;
2-(4-{4-[(2-bromophenyl)methyl]piperidyl}piperidyl)-1,3-dimethoxybenzene;
3-(4-{4-[(2-bromo-5-methoxyphenyl)methyl]piperidyl}piperidyl)-6-chloropyridazine;
1-(4-{4-[(2,5-difluorophenyl)methyl]piperidyl}piperidyl)-4,5-dimethoxy-2-methylbenzene;
1-(4-{4-[(2-bromo-5-fluorophenyl)methyl]piperidyl}piperidyl)-4,5-dimethoxy-2-methylbenzene;
1-(4-{4-[(2,5-dichlorophenyl)methyl]piperidyl}piperidyl)-4,5-dimethoxy-2-methylbenzene;
2-(4-{4-[(2-bromophenyl)methyl]piperidyl}piperidyl)-1,3,5-trimethoxybenzene;
5-(4-{4-[(2-bromophenyl)methyl]piperidyl}piperidyl)-2-methoxypyridine;
5-(4-{4-[(2-chlorophenyl)methyl]piperidyl}piperidyl)-2-methoxypyridine;
5-(4-{4-[(2,5-difluorophenyl)methyl]piperidyl}piperidyl)-2-methoxypyridine;
5-(4-{4-[(2-bromo-5-fluorophenyl)methyl]piperidyl}piperidyl)-2-methoxypyridine;
5-(4-{4-[(2,5-dichlorophenyl)methyl]piperidyl}piperidyl)-2-methoxypyridine;
3-(4-{4-[(2,5-difluorophenyl)methyl]piperidyl}piperidyl)-4-methoxybenzenecarbonitrile;
4-methoxy-3-(4{4-[(3-methoxyphenyl)methyl]piperidyl}piperidyl)benzenecarbonitrile;
3-(4-{4-[(2-bromo-5-fluorophenyl)methyl]piperidyl}piperidyl)-4-methoxybenzenecarbonitrile;
1-(4-{4-[(2,5-dichlorophenyl)methyl]piperidyl}piperidyl)-2,4,5-trimethoxybenzene;
8-(4-{4-[(2,5-dichlorophenyl)methyl]piperidyl}piperidyl)-7-methoxy-2 H,3 H,4 H-benzo[b]1,5-dioxepin.

6. A method for treating a patient suffering from depression comprising administration to the patient of a therapeutically effective antidepressant amount of a compound of claim 1.

7. A method for treating a patient suffering from depression comprising administration to the patient of a therapeutically effective antidepressant amount of a compound of claim 2.

8. A pharmaceutical composition comprising an antidepressant amount of a compound of claim 1 and a pharmaceutically acceptable carrier.

9. A pharmaceutical composition comprising an antidepressant amount of a compound of claim 2 and a pharmaceutically acceptable carrier.

* * * * *